(12) United States Patent
Lee

(10) Patent No.: US 7,749,548 B2
(45) Date of Patent: Jul. 6, 2010

(54) COMPOSITE FOR THE IMPROVEMENT OF THE SMELL OF THE ARMPIT

(75) Inventor: Sung-Nack Lee, Seongnam-Si (KR)

(73) Assignee: Ajou Medics Co., Ltd., Seoul (KR)

( * ) Notice: Subject to any disclaimer, the term of this patent is extended or adjusted under 35 U.S.C. 154(b) by 423 days.

(21) Appl. No.: 10/562,152

(22) PCT Filed: Jul. 16, 2004

(86) PCT No.: PCT/KR2004/001772

§ 371 (c)(1),
(2), (4) Date: Feb. 21, 2008

(87) PCT Pub. No.: WO2005/007180

PCT Pub. Date: Jan. 27, 2005

(65) Prior Publication Data

US 2008/0193570 A1 Aug. 14, 2008

(51) Int. Cl.
*A61K 36/82* (2006.01)
*A61K 36/886* (2006.01)
*A61K 36/48* (2006.01)
*A61K 36/00* (2006.01)

(52) U.S. Cl. .................. 424/729; 424/744; 424/757; 424/725

(58) Field of Classification Search .................. None
See application file for complete search history.

(56) References Cited

U.S. PATENT DOCUMENTS

| | | | | |
|---|---|---|---|---|
| 4,898,727 A | * | 2/1990 | Osada et al. | 424/76.1 |
| 4,906,454 A | * | 3/1990 | Melanson et al. | 424/47 |
| 5,525,331 A | * | 6/1996 | Betts | 424/65 |
| 5,770,187 A | * | 6/1998 | Hasebe et al. | 424/69 |
| 5,902,572 A | * | 5/1999 | Luebbe et al. | 424/66 |
| 6,096,298 A | * | 8/2000 | Swaile | 424/65 |
| 6,174,521 B1 | * | 1/2001 | Li et al. | 424/65 |
| 6,344,218 B1 | * | 2/2002 | Dodd et al. | 424/605 |
| 6,403,071 B1 | * | 6/2002 | Scavone et al. | 424/65 |
| 2004/0009244 A1 | * | 1/2004 | Kim et al. | 424/729 |
| 2004/0024055 A1 | * | 2/2004 | Hahm et al. | 514/461 |

FOREIGN PATENT DOCUMENTS

| | | | |
|---|---|---|---|
| JP | 07194683 | * | 8/1995 |
| JP | 09-099045 A | | 4/1997 |
| JP | 2000079158 | * | 3/2000 |
| JP | 2002080335 | * | 3/2002 |
| JP | 2003081801 | * | 3/2003 |
| KR | 1994-0000775 B1 | | 1/1994 |
| KR | 1996-0002195 B1 | | 2/1996 |
| KR | 1996-0007878 B1 | | 6/1996 |
| KR | 2000-0002239 A | | 1/2000 |
| KR | 2001-0001476 A | | 1/2001 |
| KR | 2001-0025644 A | | 4/2001 |
| KR | 2001-0091645 A | | 10/2001 |
| KR | 2002029455 | * | 4/2002 |
| KR | 2002030979 | * | 4/2002 |
| KR | 2003-0009578 A | | 2/2003 |
| KR | 2003-0043302 A | | 6/2003 |
| KR | 2003-0044306 A | | 6/2003 |

OTHER PUBLICATIONS

Urabe, K. et al., "Effects of Houttuyniae cordata and refinery final molasses on the development of offensive odor in porcine small intestine during storage" In; J. Nutr. Sci Vitaminol (Tokyo). 1994; 40(1): 63-71.

Lukacs, V. A. et al., "Antiperspirants and deodorants—ingredients and evaluation" In; Derm. Beruf. Umwelt. 1989; 37(2): 53-57.

* cited by examiner

*Primary Examiner*—Christopher R. Tate
(74) *Attorney, Agent, or Firm*—Birch, Stewart, Kolasch & Birch, LLP

(57) ABSTRACT

The present invention relates to a composition comprising ethanol, polyol, salicylic acid, triclosan, allantoin, licorice acid or its di-alkali metallic salt, dl-camphor, houttynia cordata extract, green tea extract, and aloe extract as main ingredients and water and perfume essence as auxiliary ingredients. The present composition has excellent elimination effect of offensive odors caused by sweat.

3 Claims, 2 Drawing Sheets p : positive control.  n : negative control.  Am : ampicillin.  Ba : Bacitracin.  S : sample a = The Composition of the present Invention     b = Product of "A" company     c = Product of "B" company

COMPOSITE FOR THE IMPROVEMENT OF THE SMELL OF THE ARMPIT

DETAILED DESCRIPTION OF THE INVENTION

Technical Field

Figure 1:
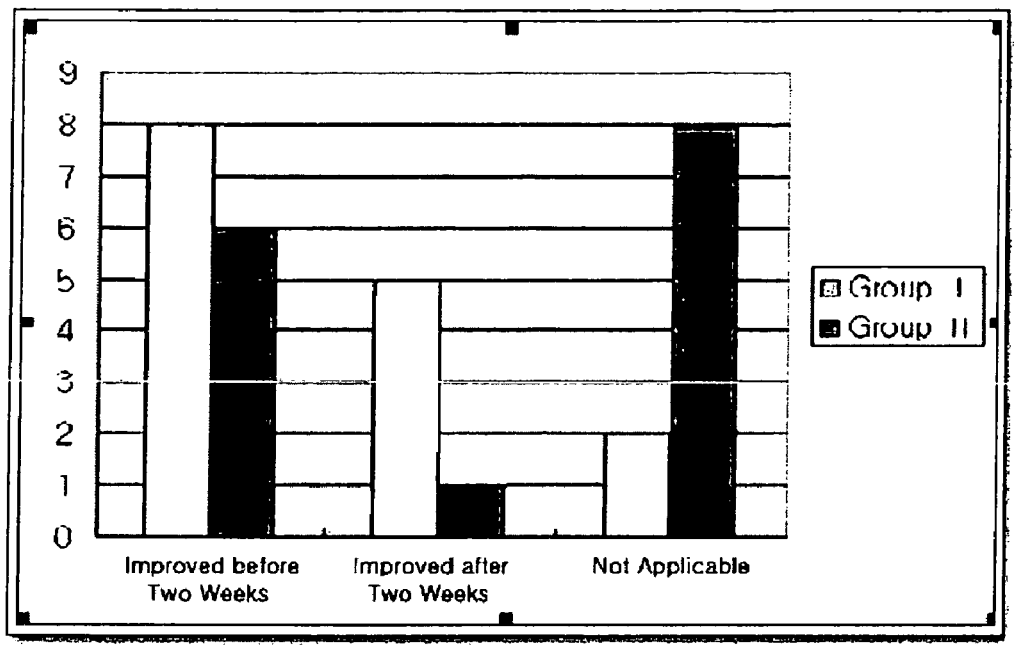
FIG. 1 is a graph showing the initial stage to improve the symptoms out of Group I & II.

This Invention relates to a unique composition which effectively eliminate offensive odors caused by sweat.

Background Art

There are approximately two millions of sweat gland covering a human body, which are mostly from "ecrine" sweat glands secreting transparent liquid with no color and smell but with little salt.

But "apocrine" sweat glands scattered in armpits, bosom, pubis and anal area secrete not only sweat but also decapitate cells out of gland's wall.

The proteinous part of the cell is dissolved by bacteria thereof as a biological process, which generates bad odors as a result of being rotten. This invention in the light of said phenomena has been approached to eradicate basic bacteria with prior emphasis.

The conventional methods has been so far passively controlled by such means as bathing and or spraying deodorant, which have not been effective and/or satisfactory.

It was quite recent that surgical operation has been imported to eliminate apocrine glands with laser mostly located in armpits, which requires expensive cost and timely burden with limited social activities after operation. Another problem is that these apocrine glands are widely distributed beside armpits, i.e. pubis and bosom area, enforcing limited surgical operation.

Sweat bromidrosis is generally defined as offensive exciting odors mainly out of armpits by secretion of apocrine glands, initiating after puberty with active secretory function, restricting particularly young women in their social activities.

This bromodrosis can be minimized by reducing bacterial flora and secretion of apocrine glands, and they do generally wash with antibiotic soap, apply antibiotics and spray perfumes, or use cosmetics controlling perspiration.

People in our country are sensitive enough even against light sweat bromidrosis, and they prefer to treat it by non-operational method, while this kinds of conventional methods have not improved it.

TECHNICAL SOLUTION OF THE INVENTION

The object of the present invention is to provide a composition which effectively treat sweat bromidrosis.

This invention relates to a composition comprising ethanol, polyol, salicylic acid, triclosan, allantoin, licorice acid or its di-alkali metallicsalt, dl-camphor, houttynia cordata extract, green tea extract, and aloe extract as main ingredients and water and perfume essence as auxiliary ingredients. The present composition has excellent elimination effect of offensive odors caused by sweat compared with conventional previous products.

DISCLOSURE OF THE INVENTION

The present invention is to provide a composition which effectively treat sweat bromidrosis.

This invention relates to a composition comprising ethanol, polyol, salicylic acid, triclosan, allantoin, licorice acid or its di-alkali metallic salt, dl-camphor, houttynia cordata extract, green tea extract, and aloe extract as main ingredients and water and perfume essence as auxiliary ingredients.

Licorice acid or its di-alkali metallic salt used in the present invention may be licorice acid, dipotassium glycyrrhizinate and disodium glycyrrhizinate, which can be extracted out of licorice or local products may be utilized.

The perfume essence used in the present invention may be selected from the group consisting lavenda oil, orange oil, lemon essence, anisol, eugenol, l-carbon, cumarine, geraniol, citral, citronelle, vaniline, nona lactone, borneol, maltol, menthol, limonene, chamonile oil, clarysage oil, bergamot oil, mandarine oil, rosemary oil, laurel oil, and or other essence oil.

As for polyols used in the present invention, it may be one of the polyols selected from the group consisting ethylene glycol, propylene glycol, butylene glycol and glycerine.

The composition of the present invention comprises 20.0~80.0 weight parts of ethanol, 5.0~10.0 weight parts of polyols, 0.01~0.50 weight parts of Licorice acid or its di-alkali metallic salt, 0.1~0.5 weight parts of salicylic acid, 0.1~0.5 weight parts of triclosan, 0.1~0.5 weight parts of perfume essence, 0.1~0.3 weight parts of allantoin, 0.01~0.1 weight parts of dl-camphor, 0.01~0.1 weight parts of saururus extract, 0.01~1.0 weight parts of green tea extract, 0.01~1.0 weight parts of aloe extract, and an adequate quantity of distilled water or purified water. Ethanol is generally utilized as a synthetic drink, solvent, fuel, anti-freezer or intermediate of organic synthesis and highly concentrated ethanol is used as sterilizer.

Polyols is a raw material of synthetic fibers, cold-proof freezer and moisturizer.

Salicylic acid is used for intermediate material of various dyes, preservatives, exfoliant or preparation of skin diseases.

Triclosan is used for anti-bacterial pr preservative agent. Allatoin is an extract extracted from comfrey root and is used to expedite histologic growth and is known to have weak bactericidal action and to improve skin resistance action.

Licorice acid or di-alkaline metallic salt is known to have anti-allergic and anti-inflammation action.

Saururus is a prennial herb belonging to Saururus chinensis with its botanical name of Houttuynia Cordata and is known to have effects such as counteracting poison, relaxing bowels, blood cleaning, and anti-bactericidal.

Green tea extract is au extract extracted from green tea wath water and contains polyphenols, catechin, etc., which is reported effective for anti-oxidation, cholesterol degrading, controlling fatty acid of triglyceride, anti-tumor, skin beauty, corpulencerestraint, heavy metal eradication, and lowering of blood pressure.

Aloe extract is an extract extracted from Aloe with water and is noted for anti-inflammation, anti-biosis, stomachal protection, promoting blood circulation, skin moisturizing or immunity regulation action. Above ingredients have not been reported to have sweat bromidrosis.

The present inventors carried out experiments for a long time, found out the facts that the present composition has an excellent effect for sweat bromidrosis and accomplished the present invention.

The composition of the present invention can be prepared as a cosmetic hair tonic of spray type to treat blemish skin of puberty generation, and caring clean scalp. When extracts of saururus and green tea are mixed with such anti-clogs as salicylic acid of BHA, it will control exceeding sebum secretion to prevent skin seborrhea with effective restraint of microorganisms' counteraction on skin.

It is therefore proved that spraying above-said tonic in such areas as armpit and toes with many apocrine glands stops development of bad odors by the action of anti-microorganism.

It is generally understood that our folks are sensitive enough to respond to sweat odors of weak extent, preferring to a treatment of non-operational method rather than that of surgical operation. Particularly western folks have much more bromidrosis than oriental people.

The present invention is to objectively confirm the effects of the composition of the present invention as mean of non-operational method.

| General example | |
| --- | --- |
| Ethanol | 20.0~80.0 wt. parts |
| Polyol | 5.0~10.0 wt. parts |
| Salicylic Acid | 0.1~0.5 wt. parts |
| Triclosan | 0.1~0.5 wt. parts |
| Perfume essence | 0.01~0.1 wt. parts |
| Allatoin | 0.1~0.3 wt. parts |
| Glycyrrhizinic Acid or Di-alkaline metallic salt | 0.01~0.2 wt. parts |
| dl-camphor | 0.01~0.1 wt. parts |
| Saururus extract | 0.01~0.1 wt. parts |
| Green tea extract | 0.01~0.1 wt. parts |
| Aloe extract | 0.01~0.1 wt. parts |
| Purified water or Distilled water | 5.0~30.0 wt. parts |

A tonic solution of spray type was prepared by blending and dissolving the above ingredients in a conventional method.

| Example 1 | |
| --- | --- |
| Ethanol | 80.0 wt. parts |
| 1,3-Butylene glycol | 8.0 wt. parts |
| Salicylic Acid | 0.48 wt. parts |
| Triclosan | 0.30 wt. parts |
| Allatoin | 0.05 wt. parts |
| Dipotassium glycyrrhizinate | 0.05 wt. parts |
| dl-camphor | 0.02 wt. parts |
| Saururus extract | 0.01 wt. parts |
| Green tea extract | 0.01 wt. parts |
| Aloe extract (1:1) | 0.01 wt. parts |
| Lavender oil | 0.05 wt. parts |
| Purified water or Distilled water | 10.89 wt. parts |

A tonic solution of spray type was prepared by blending and dissolving the above ingredients in a conventional method.

| Example 2 | |
| --- | --- |
| Ethanol | 70.0 wt. parts |
| Etylene glycol | 8.0 wt. parts |
| Salicylic Acid | 0.5 wt. parts |
| Triclosan | 0.30 wt. parts |
| Allatoin | 0.1 wt. parts |
| Dipotassium glycyrrhizinate | 0.1 wt. parts |
| dl-camphor | 0.02 wt. parts |
| Saururus extract | 0.01 wt. parts |
| Green tea extract | 0.01 wt. parts |
| Aloe extract (1:1) | 0.01 wt. parts |
| Lavender oil | 0.05 wt. parts |
| Purified water or Distilled water | 10.89 wt. parts |

A tonic solution of spray type was prepared by blending and dissolving the above ingredients in a conventional method.

| Example 3 | |
| --- | --- |
| Ethanol | 75.0 wt. parts |
| Glycerine | 8.0 wt. parts |
| Salicylic Acid | 0.48 wt. parts |
| Triclosan | 0.50 wt. parts |
| Allatoin | 0.05 wt. parts |
| Dipotassium glycyrrhizinate | 0.05 wt. parts |
| dl-camphor | 0.02 wt. parts |
| Saururus extract | 0.03 wt. parts |
| Green tea extract | 0.03 wt. parts |
| Aloe extract (1:1) | 0.02 wt. parts |
| Clary sage oil | 0.01 wt. parts |
| Lavender oil | 0.02 wt. parts |
| Purified water or Distilled water | 10.89 wt. parts |

A tonic solution of spray type was prepared by blending and dissolving the above ingredients in a conventional method.

| Example 4 | |
| --- | --- |
| Ethanol | 80.0 wt. parts |
| Propyleneglycol | 8.0 wt. parts |
| Salicylic Acid | 0.5 wt. parts |
| Triclosan | 0.30 wt. parts |
| Allatoin | 0.1 wt. parts |
| Dipotassium glycyrrhizinate | 0.1 wt. parts |
| dl-camphor | 0.02 wt. parts |
| Saururus extract | 0.01 wt. parts |
| Green tea extract | 0.01 wt. parts |
| Aloe extract (1:1) | 0.01 wt. parts |
| Citronelle | 0.01 wt. % |
| Purified water or Distilled water | 10.89 wt. parts |

A tonic solution of spray type was prepared by blending and dissolving the above ingredients in a conventional method.

| Example 5 | |
| --- | --- |
| Ethanol | 80.0 wt. parts |
| Propyleneglycol | 8.0 wt. parts |
| Salicylic Acid | 0.5 wt. parts |
| Triclosan | 0.30 wt. parts |

-continued

| Example 5 | |
|---|---|
| Allatoin | 0.1 wt. parts |
| Glycyrrhizic acid | 0.1 wt. parts |
| dl-camphor | 0.02 wt. parts |
| Saururus extract | 0.01 wt. parts |
| Green tea extract | 0.01 wt. parts |
| Aloe extract (1:1) | 0.01 wt. parts |
| Rosemary oil | 0.01 wt. parts |
| Purified water or Distilled water | 10.89 wt. parts |

A tonic solution of spray type was prepared by blending and dissolving the above ingredients in a conventional method.

| Example 6 | |
|---|---|
| Ethanol | 80.0 wt. parts |
| Propyleneglycol | 8.0 wt. parts |
| Salicylic Acid | 0.5 wt. parts |
| Triclosan | 0.30 wt. parts |
| Allatoin | 0.1 wt. parts |
| Disodium glycyrrhizinate | 0.1 wt. parts |
| dl-camphor | 0.02 wt. parts |
| Saururus extract | 0.01 wt. parts |
| Green tea extract | 0.01 wt. parts |
| Aloe extract (1:1) | 0.01 wt. parts |
| Lemon essence | 0.01 wt. parts |
| Purified water or Distilled water | 10.89 wt. parts |

A tonic solution of spray type was prepared by blending and dissolving the above ingredients in a conventional method.

Experimental Example 1

I. Objects and Method of Research

1. Application of Medical Treatment Composition of Example 1

2. Object of Research
   (1) Establishment of Objective Group
   A) Principle
   1) Sanitary cottons are kept in both armpits for ten minutes by two medical doctors' inspection of armpit odor for classification of 4 grades.
   "minimal" is almost smell-less;
   "mild" is available smell within distance of 15 cm;
   "moderate" is further than distance of 15 cm; and
   "severe" is beyond the distance of 30 cm.
   2) Volunteers are selected from the group who can smell the ordor of sweat bromidrosis by sanitary cotton method and who smell over "mild" class.
   B) Selective method and criteria
   1) All the examinees were explained the purpose, content, and tonic solution of spray type and the experiment was carried out with volunteers who agree to join the experiment voluntarily.
   2) Those who are sensitive to acne medicine, those who take medical preparation due to systemic diseases, psychotropics, or physically and mentally handicapped are exempted for this experiment.
   3) Fifteen volunteers who were fitted for the above criteria and smell over "mild" class were selected.
   (2) grouping: It was divided into two groups according to overall research object and test samples:
   1) Individual Group
   Group I Test group with the composition of example 1
   Group II: Control group with 80% ethanol
   2) Final individual Group
   Those who do not follow directions and those who are not followed up till the end of the experiment were exempted for our precise analysis. But no one was exempted during the test examination period. Fifteen (15) volunteers went through from the beginning for our successful experiment. All the data of 15 volunteers were analyzed.

3. Experimental Method
   (1) Experimental period and judgment
   Applying the present composition and ethanol of 80% carried out for four (4) weeks beginning from April 2003 and the judgment was made by the time of final application.
   (2) Application Method
   The composition of example 1 and ethanol of 80% were sprayed twice a day in both armpits during the period of four weeks. No one was allowed to use other cosmetics, perfume, and anti-germ soap not to influence any result.

4. Judgement of the Result
   (1) Analysis of applying result with Example 1
   A) Subjective methods:
   Subjective judgment of odor degree through individual queries, which include:
   1) basic personal status of the participant;
   2) odor level before the application of the composition;
   3) faithfulness of applying method;
   4) degrees of improvement of odor level during the period of application; and
   5) any side effects.
   B) Objective Method
   Measurements of axillary odor were decided according to the smell degree by means of sanitary cotton, which were classified into four (4) grades. Namely, sanitary cottons are kept in both armpits for ten minutes by two medical doctors' inspection of armpit odor for classification of 4 grades as shown in the Table 1:

TABLE 1

| Grade of axillary odor | |
|---|---|
| Grade | Definition |
| Minimal | Almost no odor |
| Mild | Odor is detected within 15 cm distance |
| Moderate | Odor is detected over 15 cm distance |
| Severe | Odor is detected over 30 cm distance |

(2) Judgment of Results: After two (2) and four (4) weeks of the application of the composition, the odor grades were judged by means of sanitary cottons from both armpits of the participants.

II. Results

1. Analysis of the applying result:
   (1) Subject Evaluation
   A) Basic status of participating individuals
   1) Age Distribution: Age group are men and women of 26 years old on an average.

2) Sex Distribution: Out of total 15 applicants 11 are men (73%), while 4 are women (27%).

B) Odor Status prior to application: Ten (10) applicants replied "moderate", and five (5) "severe" to questions of odor grades, which mean "serious" to some extent for the participants as shown in the Table 2.

TABLE 2

Odor status prior to the application of the composition

| Grade | Total (Mean) |
|---|---|
| Minimal | None (0%) |
| Moderate | 10 persons (67%) |
| Severe | 5 persons (33%) |

C) Faithfulness of application method: In addition to our purpose to exclude those who don't follow directions, there were queries to reflect their adaptability of the composition. Those were classified in convenience as percentage and in order to objectify the results, the following queries were raised.

1) 100% applied Applied twice a day.
2) 75% applied Missed two or three days during 4 weeks.
3) 50% applied Applied half of 4 weeks.
4) 25% applied Applied one or two days.
5) 0% Applied once or twice.

The results were shown in the Table 3.

TABLE 3

| Faithfulness of applying method | Total (Mean) |
|---|---|
| 100% | 11 person (73%) |
| 75% | 3 person (20%) |
| 50% | 1 person (7%) |
| 25% | None (0%) |
| 0% | None (0%) |

In order to fix the used quantity of the composition during the period of 4 weeks, the measurement the volume (V) of the composition was evaluated in five steps as below, provided that faithful application of 48 times based on twice a day consumes 10 ml.

The results were shown in the Table 4.

TABLE 4

| | Total (Mean) |
|---|---|
| Top consumption (5 ml < V < 15 ml) | 10 persons (67%) |
| Medium + (5 ml < V < 20 ml or 5 ml < V < 20 ml) | 3 persons (20%) |
| Medium (20 ml < V < 25 ml) | 1 persons (7%) |
| Medium − (25 ml < V < 30 ml) | None (0%) |
| Low (30 ml < V) | None (0%) |

D) Percentage of Improvement by Self-Assessment

The degree of improvement of ordor after 4 weeks were measured by self-assessment. The results were shown in the Table 5. All of 15 persons replied over 50% of improvement in the experimental group, while 10 persons in comparison group expressed positive improvement and four persons' replied negative.

TABLE 5

Percentage of improvement by self-assessment

| | Group I | Group II |
|---|---|---|
| Improved 100% | 3 (20%) | 1 (7%) |
| Improved 75% | 6 (67%) | 7 (47%) |
| Improved 50% | 2 (13%) | 2 (13%) |
| Improved 25% | 0 (0%) | 1 (7%) |
| Not applicable | 0 (0%) | 4 (27%) |
| Got worse | 0 (0%) | 0 (0%) |

E) Side-Effects

No side-effect to require medical care were reported during the period except three persons each of the two groups replied a slight tingle feel right after application, but faded away in thirty minutes. The results were shown in the Table 6.

TABLE 6

Number and percentage of side-effect

| | Group I | Group II |
|---|---|---|
| Side effect | 3 (20%) | 3 (20%) |
| No side-effect | 12 (80%) | 12 (80%) |

(2) Objective Evaluation

Measurement of axillary ordor was carried out by two medical doctors by using sanitary cottons in order to evaluate objectively as shown below

TABLE 7

Measurement of Axillary Ordor by Sanitary Cotton (Group I & II)

| Volunteers | | Initial | | after 2 weeks | | after 4 weeks | |
|---|---|---|---|---|---|---|---|
| | | doctor 1 | doctor 2 | doctor 1 | doctor 2 | doctor 1 | doctor 2 |
| KEJ | group I | mild | mild | mini | mini | mini | mini |
| | group II | mild | mild | mini | mini | mini | mini |
| KDH | group I | mod | mod | mild | mild | mini | mini |
| | group II | mod | mod | mod | mod | mod | mod |
| KBJ | group I | mod | mod | mod | mod | mild | mild |
| | group II | mod | mod | mild | mild | mild | mild |
| LSH | group I | mod | mod | mod | mod | mod | mod |
| | group II | mod | mod | mod | mod | mod | mod |
| LKC | group I | mod | mod | mild | mild | mini | mini |
| | group II | mod | mod | mod | mod | mild | mild |
| YHS | group I | mild | mild | mini | mini | mini | mini |
| | group II | mild | mild | mild | mild | mild | mild |
| KBC | group I | mod | mod | mod | mod | mild | mild |
| | group II | mod | mod | mod | mod | mod | mod |
| HYE | group I | mod | mod | mild | mild | mini | mini |
| | group II | mod | mod | mild | mild | mild | mild |
| SJB | group I | mild | mild | mild | mild | mild | mild |
| | group II | mild | mild | mild | mild | mild | mild |
| SSS | group I | mod | mod | mini | mini | mini | mini |
| | group II | mod | mod | mini | mini | mini | mini |
| LCJ | group I | mod | mod | mild | mild | mini | mini |
| | group II | mod | mod | mild | mild | mild | mild |
| CCS | group I | mild | mild | mild | mild | mini | mini |
| | group II | mild | mild | mini | mini | mini | mini |
| LSH | group I | mod | mod | mild | mild | mild | mild |
| | group II | mod | mod | mod | mod | mod | mod |
| LSY | group I | mild | mild | mild | mild | mini | mini |
| | group II | mild | mild | mild | mild | mild | mild |
| KHY | group I | mild | mild | mild | mild | mini | mini |
| | group II | mild | mild | mild | mild | mild | mild |

** Remarks: "mini" means "minimal" and "mod" means "moderate".

Result Analysis

It has been analyzed according to the beginning period of improvement and improving progress between group I and II as shown in Table 8 below.

a) Commencing period of improvement 13 persons showed improvement after 4 weeks in group I, while 7 persons in group II expressed affirmative improvement in same period of time.

b) 3 persons among 13 in group I replied positive improvement after two weeks application, and 6 persons out of 7 in group II answered the same.

TABLE 8

| Initiating Period of Improvement | | |
|---|---|---|
| | Group I | Group II |
| Within 2 weeks | 8 (53%) | 6 (40%) |
| After 2 weeks | 5 (33%) | 1 (7%) |
| Not improved | 2 (13%) | 8 (53%) |

The results of Table 8 was shown in FIG. 1.

Degree of Improvement

It has been analysed that among 13 persons whose symptoms were improved in Group I, 5 persons showed 2 stages or more of improvement, whereas in Group II among 7 persons whose symptoms were improved, only one person showed 2 stages or more of improvement. The result was shown in Table 9 below.

TABLE 9

| Degree of Improvement | | |
|---|---|---|
| | Group I | Group II |
| 2 stage or more of improvement | 5 (33%) | 1 (7%) |
| 1 stage of improvement | 8 (53%) | 6 (40%) |
| no improvement | 2 (13%) | 8 (53%) |

Figure 2:
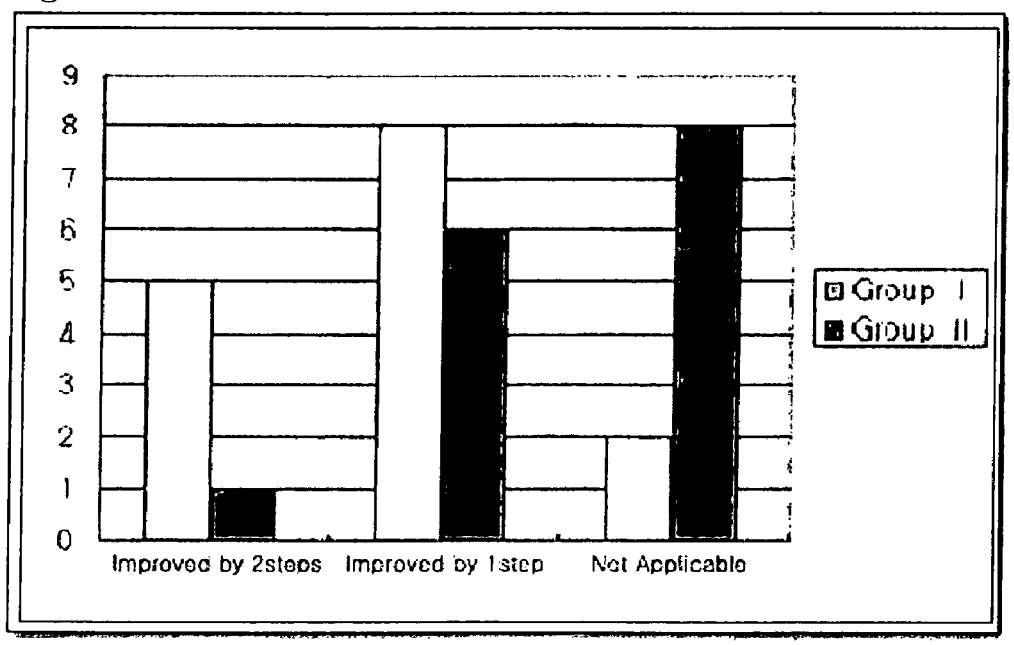
FIG. 2 a graph showing improvement ratios from Group I & II.

The results of Table 9 was shown in FIG. 2.

III. Results

This is a research to evaluate the effectiveness of this composition for those patients with sweat ill-odors.

There were total 15 volunteers for the research under right armpit as a test group I with our tonic solution and left armpit as a comparative group II with 80% ethanol in order to analyze each of its results in two weeks experiment and four weeks long test.

The effective evaluation of this composition has been undergone in the light of objective measurement of the odor grades by subjective questions and other methods, which are illustrated as below a) Group II of 80% ethanol showed improved 7 persons out of 15, while 13 persons in Group I of our tonic solution showed betterments.

b) One person among 7 in Group II had betterment by two steps, and 5 persons out of 13 showed improvement by two steps.

This results proves that the composition of this invention is far more effective that that of 80% ethanol with temporary sterilizing job, self-explaining basic effective treatment of osmidrosis by controlling counteraction of microorganism.

It is true that comparisons with existing products haven't been made for contrast evaluation, but there has been no research as this to classify the grades of offensive odors in terms of objectivity.

Experimental example #2 has been performed to make comparison with other products by culturing microbial germs in armpit area for comparing hemolysis.

There has been no side effect to note, except that three persons among 15 complained a slight tingle feel right after application, but faded itself away soon, which is considered to be developed for patients' adaptation.

This is a research of a clinical effectiveness on perspiration odors by the composition of this invention as a cosmetic for acne skins, which has been proved effective enough to improve osmidrosis symptoms.

Accordingly it has shown suggestive to use not only for blemish skins of puberty and cleaning scalp but also for those offensive odors.

IV. References

1. What is the best method for treating osmidrosis? Ann Plast Surg 2001 written by Park Y J and Shin M S.
2. Minimally invasive surgery for axillary osmidrosis: combined operation with CO2 laser and subcutaneous tissue remover. Dermatol Surg 1999 Nov. 25 (11) 875-9 written by Kim I H, Seo S L, and Oh C H
3. Microbial research and its genetic observation on skin surface of axillary osmidrosis written by Gook J P, Lee S C, Jeon I G, & Kim Y P 28: 559 564, 19904.
4. Clinical Observation on surgical operation of osmidrosis by deietinghypodermic cells written by Kim Y D, Moon E C, & Kim S N 29:65 71, 1991

Experimental Example 2

1) Measurement of Hemolytic Reaction

Experimental comparison has been performed among our composition of example 1 and two products on sale in regards to such axillary microbial germs as Acinetobacter 2334, Brevibacterium sp. 1838, and Brevibacterium sp. 1839, and *Corynebacterium minutissimum*.

2) Acinetobacter 2334, *Brevibacterium* s. 1838, *Brevibacterium* sp. 1839, and *Corynebacterium minutissimum* were cultured respectively in a media (40 gram/liter, pH 7.2) made of Difco TM Tryptic Soy Agar (BD, catalog #236950) for 48 hours at the temperature of 37° C.

As the positive control of hemolytic examination, a solution containing erythromycin (Aknemycin), ampicilin (BBL tm Sensi-Disc), and bacitracin (BBL tmSensi-Disc tm) were used, while a solution without erythromycin was applied for the negative control.

Figure 3:
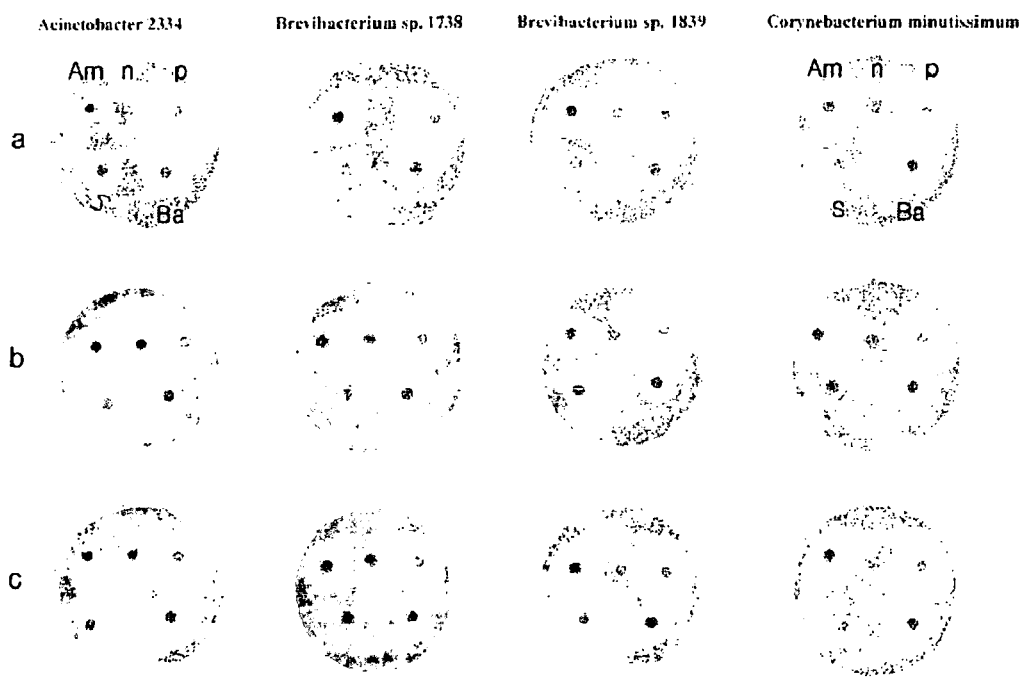
FIG. 3 are pictures comparing haemolysis effects of the present composition with other existing products.

The products to be examined were placed on a filter paper inoculated with 20 micro-liters inside a germ-free hood of cell cultivation, and it was put on an agar culture medium with designated bacteria, which were cultivated 48 hours in a conventional incubator with air. A photo was then taken after measuring the diameter of hemolytic part, which shows on the FIG. 3, in which a is the result showing the effect of the present composition; b and c are the results showing the effects of those products of A & B companies.

It was accordingly concluded that the composition of the present invention is much more excellent hemolytic than those products of A & B companies.

INDUSTRIAL APPLICABILITY

As confirmed in the experimental example 1 and 2, the composition of the present invention has an excellent effect against sweat osmidrosis.

The invention claimed is:

1. A composition for improving sweat osmidrosis comprising:
    ethanol, polyol, salicylic acid, triclosan, allantoin, a licorice acid or its di-alkali metallic salt, dl-camphor, *Houttuynia cordata* extract, green tea extract, and aloe extract as main ingredients and water and perfume essence as auxiliary ingredients, the composition comprising:
    20.0-80.0 weight parts of ethanol,
    5.0-10.0 weight parts of polyols,
    0.01-0.50 weight parts of the licorice acid or its di-alkali metallic salt,
    0.1-0.5 weight parts of salicylic acid,
    0.1-0.5 weight parts of triclosan,
    0.1-0.5 weight parts of perfume essence,
    0.1-0.3 weight parts of allantoin,
    0.01-0.1 weight parts of dl-camphor,
    0.01-0.1 weight parts of *Houttuynia cordata* extract,
    0.01-1.0 weight parts of green tea extract, 0.01-1.0 weight parts of aloe extract, and
    5.0-30.0 weight parts of distilled water or purified water.

2. A composition for improving apocrine sweat gland osmidrosis, consisting essentially of:
    20.0-80.0 weight parts of ethanol,
    5.0-10.0 weight parts of polyols,
    0.01-0.50 weight parts of a licorice acid or its di-alkali metallic salt,
    0.1-0.5 weight parts of salicylic acid,
    0.1-0.5 weight parts of triclosan,
    0.1-0.5 weight parts of perfume essence,
    0.1-0.3 weight parts of allantoin,
    0.01-0.1 weight parts of dl-camphor,
    0.01-0.1 weight parts of *Houttuynia cordata* extract,
    0.01-1.0 weight parts of green tea extract,
    0.01-1.0 weight parts of aloe extract, and
    5.0-30.0 weight parts of distilled water or purified water.

3. A composition for improving apocrine sweat gland osmidrosis, consisting of:
    20.0-80.0 weight parts of ethanol,
    5.0-10.0 weight parts of polyols,
    0.01-0.50 weight parts of a licorice acid or its di-alkali metallic salt,
    0.1-0.5 weight parts of salicylic acid,
    0.1-0.5 weight parts of triclosan,
    0.1-0.5 weight parts of perfume essence,
    0.1-0.3 weight parts of allantoin,
    0.01-0.1 weight parts of dl-camphor,
    0.01-0.1 weight parts of *Houttuynia cordata* extract,
    0.01-1.0 weight parts of green tea extract,
    0.01-1.0 weight parts of aloe extract, and
    5.0-30.0 weight parts of distilled water or purified water.

* * * * *